United States Patent
Blaschke et al.

(10) Patent No.: US 9,784,704 B2
(45) Date of Patent: Oct. 10, 2017

(54) NON-INVASIVE MEASUREMENT OF DIELECTRIC PROPERTIES OF A SUBSTANCE

(71) Applicant: Parelectrics UG (haftungsbeschränkt), Berlin (DE)

(72) Inventors: Tobias Blaschke, Berlin (DE); Klaus K. Kramer, Berlin (DE); Dierk Lesemann

(73) Assignee: Parelectrics UG (Haftungsbeschrankt), Berlin (DE)

( * ) Notice: Subject to any disclaimer, the term of this patent is extended or adjusted under 35 U.S.C. 154(b) by 379 days.

(21) Appl. No.: 14/382,484

(22) PCT Filed: Mar. 4, 2013

(86) PCT No.: PCT/EP2013/054271
§ 371 (c)(1),
(2) Date: Sep. 2, 2014

(87) PCT Pub. No.: WO2013/128033
PCT Pub. Date: Sep. 6, 2013

(65) Prior Publication Data
US 2015/0109004 A1    Apr. 23, 2015

(30) Foreign Application Priority Data
Mar. 2, 2012 (EP) .................... 12157988

(51) Int. Cl.
*G01N 27/22* (2006.01)
*G01N 15/06* (2006.01)
(Continued)

(52) U.S. Cl.
CPC ....... *G01N 27/228* (2013.01); *G01N 15/0656* (2013.01); *G01N 27/221* (2013.01); *G01N 33/49* (2013.01); *G01N 2015/0053* (2013.01)

(58) Field of Classification Search
CPC .. G01N 33/49; G01N 27/228; G01N 15/0656; G01N 27/22; G01N 2015/0053; G01N 27/223
See application file for complete search history.

(56) References Cited

U.S. PATENT DOCUMENTS

| 4,240,028 A | 12/1980 | Davis, Jr. |
| 5,224,769 A * | 7/1993 | Holbrook ............. G01N 27/223 324/664 |

(Continued)

FOREIGN PATENT DOCUMENTS

| DE | 102006036188 A1 | 2/2008 |
| EP | 0268399 A2 | 5/1988 |

(Continued)

*Primary Examiner* — Jermele M Hollington
*Assistant Examiner* — Zannatul Ferdous
(74) *Attorney, Agent, or Firm* — Ryan, Mason & Lewis, LLP

(57) ABSTRACT

The invention pertains to an apparatus and a method for determining a dielectric property of a first substance in a composition in a non-invasive manner. The composition includes at least the first substance to be measured and a second substance. The method uses and apparatus includes a capacitor for creating a field into which the composition can be introduced at least in part, where the capacitor is part of an oscillator circuit, and the oscillator circuit is coupled to a device for determining the resonance frequency of the oscillator circuit. The capacitor includes a layer of a non-conducting material such that the composition, when introduced at least in part into the field of the capacitor, does not come into an electrical contact with the electrodes of the capacitor.

10 Claims, 12 Drawing Sheets

(51) Int. Cl.
*G01N 33/49* (2006.01)
*G01N 15/00* (2006.01)

(56) References Cited

U.S. PATENT DOCUMENTS

| | | |
|---|---|---|
| 6,014,029 A | 1/2000 | Soto et al. |
| 6,028,433 A | 2/2000 | Cheiky-Zelina et al. |
| 2001/0019271 A1 | 9/2001 | Scott et al. |
| 2011/0093212 A1 | 4/2011 | Herrmann et al. |
| 2011/0181304 A1* | 7/2011 | Gehrig ................. B65B 13/025 |
| | | 324/674 |
| 2013/0119512 A1* | 5/2013 | Malhotra .......... H01L 27/10852 |
| | | 257/532 |

FOREIGN PATENT DOCUMENTS

| | | |
|---|---|---|
| EP | 12157988 | 7/2012 |
| WO | PCT/EP2013/054271 | 6/2013 |

* cited by examiner (Prior Art)

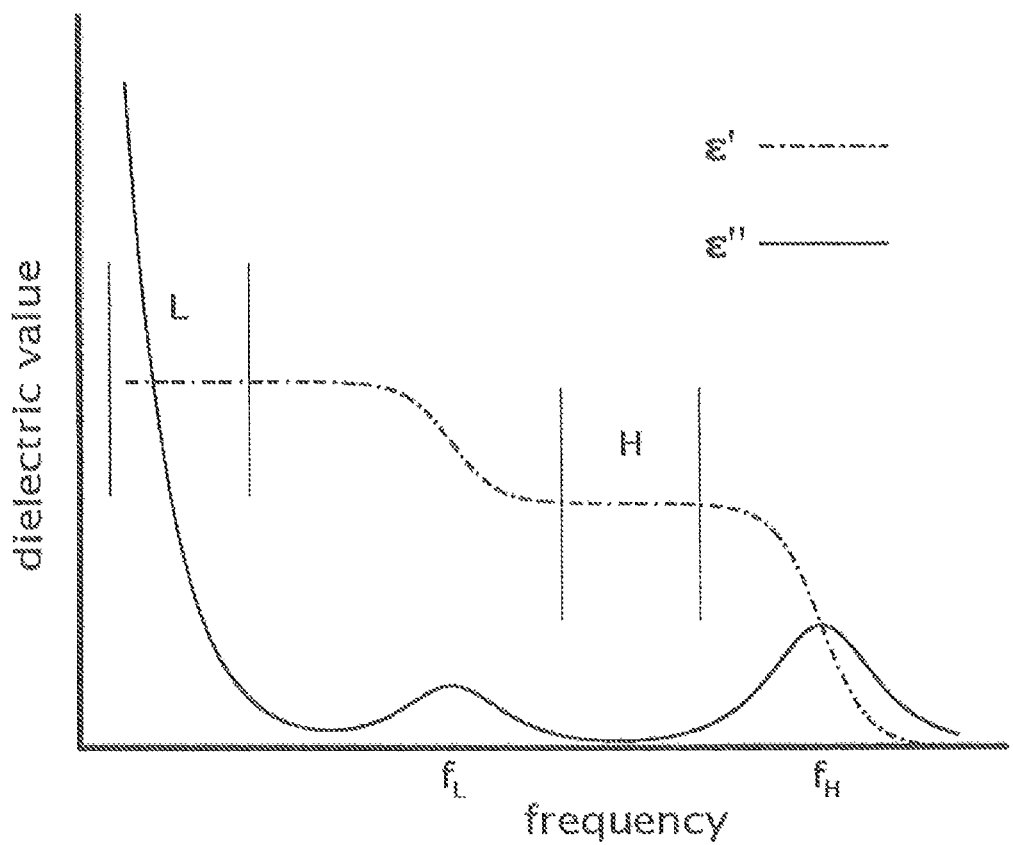

NON-INVASIVE MEASUREMENT OF DIELECTRIC PROPERTIES OF A SUBSTANCE

FIELD OF INVENTION

The invention pertains to a method and an apparatus for the non-invasive measurement of dielectric properties and a method for the non-invasive measurement of dielectric properties.

BACKGROUND OF THE INVENTION

There are many applications for which physical properties of a certain substance mixed with or included in another substance need to be determined to high accuracy. For example, in medical treatment, the density of particles in aqueous solutions has to be known in order to assure proper treatment or proper diagnosis. Also, it is needed to adjust the composition of a dialysate when a patient's renal deficiencies have to be compensated. Moreover, the volume percentage of water in a patient's blood has to be measured and monitored.

From the state of the art, methods and devices are known that are based on the principle of driven oscillations, i.e. they need an external transmitter and receiver. Such systems and devices, however, are disadvantageous.

Thus, the problem underlying the present invention was to provide a means of determining properties of a known particle kind within a composition of different kind of particles by using a more precise method that can be performed in a non-invasive manner.

SUMMARY OF THE INVENTION

This problem is solved by the present invention.

The inventors have found a means for determining dielectric properties of a substance in a composition or mixture of substances, such as particle density, mobility, and electric conductivity of said substance. This is achieved by measuring the resonance frequency of an oscillator circuit when the composition or mixture of substances is introduced into the electric field of a capacitor that is part of an oscillator circuit. From the measured resonance frequency, the dielectric properties of the substance can be determined, i.e. the particle density, the mobility, and the electric conductivity of said substance.

This is based on the fact that the capacitance of a capacitor can be determined by the frequency-dependent complex dielectric value of the composition in the electric field of the capacitor.

In contrast to methods known in the state of the art that are based on the principle of driven oscillations, which need an external transmitter and receiver, the present invention is based on a self-oscillating circuit that needs no external devices.

BRIEF DESCRIPTION OF THE DRAWINGS

Exemplary embodiments of the present invention will be described below in more detail, with reference to the accompanying drawings, of which:

FIG. 2 is a graph of the dielectric values of a first and a second substance of a composition versus frequency according to an embodiment of the present invention.

DETAILED DESCRIPTION OF EXEMPLARY EMBODIMENTS OF THE INVENTION

Figure 1A:
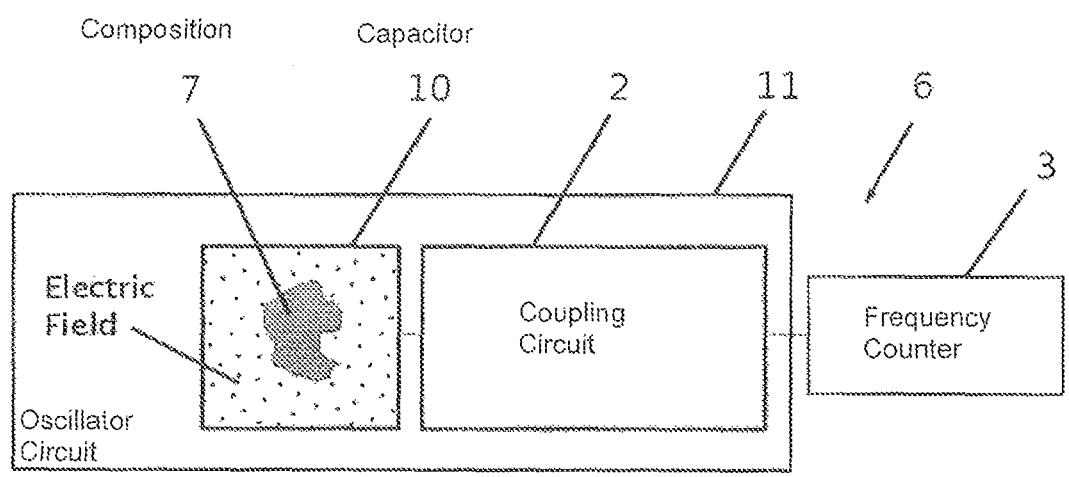
FIG. 1a shows a block diagram of an apparatus comprising an oscillation circuit including a capacitor with arbitrary geometry (allowing for measuring in stray-field or internal field) and a frequency-counter according to an embodiment of the present invention.

Exemplary embodiments of the invention will now be discussed in further detail. This invention may, however, be embodied in many different forms and should not be construed as limited to the embodiments set forth herein.

A driven oscillation is created when the signal of an external frequency-generator is fed into a resonating system. The maximum amplitude of this driven oscillation is reached when the external frequency passes through the intrinsic resonance-frequency of the system. The self-oscillating system of the present invention, in contrast, comprises an amplifier, which uses the resonance-system as a coupling path between its output and input. Such a system always oscillates at its intrinsic resonance frequency (see also FIG. 1c). This frequency directly reflects the properties of the substance to be analyzed and can be measured without further processing. A self-oscillating circuit of the present invention comprises a resonator and an amplifier.

According to the invention, the measurement of only one frequency may, in one preferred embodiment of the invention, be sufficient and it is not necessary to scan through a—possibly wide—range of frequencies for the determination. How to choose an appropriate frequency will be described later.

The substance that is to be determined regarding its dielectric properties, referred to herein also as the "first substance", needs to be known and have a dipole and/or carry a charge. The first substance can be a pure substance or a mixture of at least two substances. The first substance is preferably a liquid or a gas. The second substance can be a liquid, a gas or a solid.

The term "dielectric properties" as used herein refers to the particle density (i.e. the density of the first substance in the composition), the particle mobility of the first substance in the composition and a possible electric conductivity as well as the strength of permanent electric dipole moments of the first substance.

The term "composition", as used herein, refers to at least two different kinds of particles that are present together. The composition comprises at least the first substance, whose dielectric properties are to be determined, and a second substance, in which the first substance is contained. The term "contained" in this context means that the composition can be a real solution, a mixture of the first and the second solution or an inclusion of the first substance in at least the second substance. It is also possible that the composition comprises a liquid solution that is included in a solid as the at least second substance.

The composition may comprise different numbers of substances. For example, the composition may be a complex substance, in particular a biological composition, which may comprise hundreds of substances. Generally, the composition may comprise at least 2 substances, and possibly up to hundreds of substances, preferably 2 to 5 different substances.

Examples for biological compositions, in particular for body fluids are chosen from the group containing: blood, plasma, serum, body fluid, saliva, urine, semen, fluid from the pleural cavity, fluid from the peritoneal cavity, cerebrospinal fluid, sputum, stool, tears, sweat, lymph fluid, bronchial lavage, pleural effusion, meningeal fluid, glandular fluid, fine needle aspirates, nipple aspirates fluid, spinal fluid, conjunctival fluid, duodenal fluid, pancreatic juice, or bile.

A "capacitor", as used herein, is a passive two-terminal electrical component with two electrodes that are separated from each other. It is possible, in certain embodiments of the inventions, that one and the same electrode may be part of two capacitors. The term capacitor is used herein without regard to the geometry of the electrodes or the kind of the electrodes used. When a potential difference exists between the electrodes of the capacitor, an electric field exists.

The capacitor creates an electric field into which the composition comprising at least the first substance to be measured is brought. Changes in the properties of the material present in the capacitor field cause changes in the capacitance of the capacitor. Since the capacitor is part of a resonance circuit, changes in the capacitance of the capacitor can be measured with high precision as frequency shifts, i.e. by determining the resonance frequency of the resonance circuit with high resolution, e.g. with a resolution $\Delta f/f = 10^{-6}$ (with $\Delta f$ as the frequency shift and f the resonance frequency without the composition in the field).

The oscillator circuit is preferably a self-oscillating circuit. This means that the oscillator circuit is not based on a transmitter and a receiver, as graphically shown in FIG. 1c. Instead, the oscillating circuit of the invention comprises a capacitor and an inductor. The oscillator circuit can be realized in several ways. Preferably, the oscillating circuit comprises a multivibrator scheme or comprises a parallel-resonance circuit where capacitance and inductance are distributed over a ¼ wavelength of a coaxial-line resonator.

The present invention is superior to reflection methods that are based on circuits that comprise a transmitter for transmitting a signal and a receiver that detects the reflected signal. With such methods, small changes in amplitude of the reflected wave are measured. Such measurements, however, are far less precise as the ones of the present invention. In contrast to reflection methods that measure small differences of large amplitudes, the frequency shifts underlying the present invention can be detected with far smaller uncertainties, even as small differences of large numbers.

A general depiction of the invention in the form of a simplified electrical circuit is shown in FIG. 1a, which will be referred to in greater detail below. Such a device overcomes the poor signal to noise ratio and yields results in higher accuracy in comparison to methods based on reflection.

In a first aspect, the invention pertains to an apparatus for determining the complex dielectric property of a first substance in a composition in a non-invasive manner. "Non-invasive" means in this context that the electrodes of the capacitor are not being introduced into the composition to be measured such that a conductive contact exists between the electrodes on the one hand and the composition on the other hand. In one embodiment, the electrodes of the capacitor comprise a layer of an insulating material, such as plastic (e.g., polytetrafluorethylene, polyvinylchloride, or other suitable materials), so that the electrodes of the capacitor do not come into electrical contact with the composition when they are being introduced into a composition.

The apparatus comprises or consists of a resonance circuit with a capacitor, and a device for determining the resonance frequency of the resonance circuit that is loosely coupled to the resonance circuit such that it does not influence the frequency of the resonance circuit. The capacitor is used as part of a resonance circuit. The shift of the resonance frequency in a pre-selected frequency region (as will be explained below) reflects the influence of the dielectric parameters of interest.

The resonance circuit can have the form of a cavity-resonator, preferably a lambda/4-resonator ($\lambda$/4-resonator) that forms a standing wave. Preferably, a $\lambda$/4 resonator is magnetically coupled to the rest of the oscillating circuit.

Preferably, the apparatus comprises or consists of at least one capacitor for creating an electric field into which the composition can be introduced at least in part, and a device for determining the resonance frequency of the resonance circuit. Through the introduction of the composition into the field of the capacitor, a change of the resonance frequency of the resonance circuit is induced.

The device of the apparatus for determining the resonance frequency of the resonance circuit is a frequency counter or cymometer, and is coupled to the oscillator circuit and measures and optionally displays the oscillation frequency through a display device of the apparatus. The measured resonance frequency is used to determine the dielectric property of the first substance, as will be explained below. Any frequency counter known in the art can be used in the apparatus of the invention. The frequency counter needs to be configured to measure the frequency in the range that is chosen.

The field created by the capacitor can be separated into a main field that is located geometrically between the electrodes of the capacitor and a stray field that is located geometrically outside of the space between the electrodes of the capacitor. For example, if the capacitor is a plate capacitor with two identically sized circular electrodes positioned in parallel and opposite to each other, the cylindrical volume bordered on two sides by the two circular electrodes defines the main field. The field outside of said cylindrical volume is the stray field.

In some preferred embodiments, the apparatus contains a capacitor whose electrodes are not positioned parallel to each other, such that the measurement of the resonance frequency is performed with the composition being introduced into only the stray field, but not the main field. In other embodiments, the composition is introduced into both the main and the stray field. Using the stray field allows to perform a measurement for dielectric properties of the substance without having to destroy the material sample that is used for the measurement.

In a preferred embodiment of the apparatus, the capacitor comprises a first and a second electrode, both of which are configured such that they are electrically isolated towards the composition that is to be introduced at least in part into the field created by the capacitor. For this purpose, at least one of the electrodes of the capacitor, preferably both, comprise(s) a layer of an electrically insulating material, which prevents a direct electrical contact of the electrode with a composition that may be introduced between the two electrodes of the capacitor. In other words, such electrodes allow for contact-free introduction of a composition into the field of the capacitor. Examples of insulating materials that may envelop the electrodes are e.g. polytetrafluoroethylene, polyvinylchloride (PVC), or other suitable materials.

In a preferred embodiment of the apparatus, the apparatus comprises a circuit for generating a frequency for the resonance circuit. This circuit can be an astable multivibrator or a parallel resonance scheme in form of a cavity-resonator. The apparatus can have one or several, e.g. three, four, five, six, seven, etc. circuits.

Preferably, an astable multivibrator is used in the apparatus of the invention. The astable multivibrator is an electronic circuit used to implement the generation of oscillations. It contains two amplifying devices (transistors, electron tubes or other devices) cross-coupled by the capacitor. The circuit of the astable multivibrator is not stable, i.e. it continually switches from one state to the other.

Figure 3A:
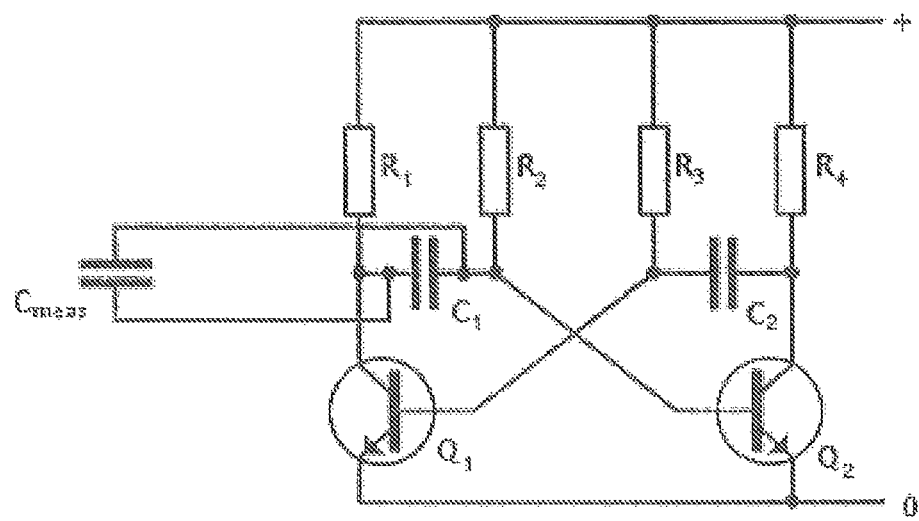
FIG. 3a shows an astable multivibrator, i.e., a regenerative circuit consisting of two amplifying stages connected in a positive feedback loop by two capacitive-resistive coupling networks to a capacitor according to an embodiment of the present invention.

In a preferred embodiment, the astable multivibrator is one as shown in FIG. 3a.

A preferred embodiment of the apparatus of the invention allows for the determination of the complex dielectric property of a first substance in a composition dependent on the distance from the electrodes. In other words, the preferred embodiment allows for the measurement of a depth profile of the dielectric property of the first substance.

For this purpose, the apparatus further comprises (i.e. besides a first capacitor as described above) at least a second capacitor for creating a second field into which the composition can be introduced at least in part. It is also possible to provide more than two capacitors, e.g. three, four, five, or more. The second capacitor (generally, each capacitor) is part of a second (generally, of a separate) oscillator circuit for measuring the dielectric property of the first substance. Further, the oscillation frequency of the second (generally, of each) capacitor is determined independently, yielding a plurality of oscillation frequencies. Preferably, the capacitors each have a different length, such that all capacitor can be operated simultaneously without interfering with each other. Further, the capacitors are preferably aligned in a coaxial fashion. On one side of the capacitors, a dielectric material is positioned that preferably makes up a plain surface that is to be placed onto the composition to be measured, containing the first substance. For this application of the apparatus, the first substance to be measured is preferably part of a solid or semi-solid composition.

Such an apparatus allows, for example, for measuring the penetration depth of a liquid in a solid, such as the water penetration in a wall of a building, e.g. a wall made of concrete.

In a preferred embodiment, the apparatus of the invention is constructed as a hand-held device.

In a further aspect, the invention pertains to the use of an apparatus as described above and herein.

Such an apparatus can be used to determine the dielectric property of a first substance in a composition, the composition comprising at least the first substance to be measured and a second substance.

The first substance of the composition is usually a liquid or a gas. The second substance of the composition is a liquid, gas, or a solid.

It is possible to measure the resonance frequency of the composition with the apparatus of the invention without any reference measurements, as long as the first substance and its dielectric value are known. Such a measurement would yield a relative value for the dielectric property.

In order to obtain an absolute figure for the dielectric property of the first substance, two measurements are needed that allow deducing from the determined values a calibration function or calibration curve. Specifically, the at least two measurements that are needed in order to establish a calibration function in the form of a line are the pure first substance, and the composition without the first substance. In case the composition consists of only two components, namely the first substance and a second substance, the pure second substance is used for the measurement.

Accordingly, in a preferred embodiment, the use of the apparatus as described above and herein, in which an absolute value of the dielectric property of the first substance is determined, further comprises the following steps: First, the resonance frequency of the resonance circuit is determined when only the first substance is introduced at least in part into the field of the capacitor. Secondly, the resonance frequency of the second oscillator circuit is determined when the composition without the first substance is introduced at least in part into the field of the capacitor. It is noted that the first and the second step can be performed in any sequence (first step before the second step or vice versa) or simultaneously, even with independent apparatuses. In a third step, the obtained values are used to determine therefrom a calibration function. When only two values are obtained, a line will result. Therefore, it is preferred to obtain more than two measurements, in particular three, four, five, ten, or more measurements to obtain a calibration function that may represent a different relation than a linear function. This calibration function is then used for determining the absolute value of the dielectric property of the first substance by comparing the measured value of the first substance as part of the composition with the calibration function.

Generally, the first substance should show a response with a difference to the other substances of the composition of at least about factor 10 (explained below in greater detail with respect to FIG. 2).

In preferred embodiments of the present invention, the apparatus as described above and herein can be used for determining from the dielectric property of the first substance the content of water as the first substance in the blood of a patient as the second substance, in particular during dialysis, the concentration of an ion as the first substance in a dialysate as the second substance, the content of ethanol as the first substance in diesel fuel as the second substance, or the inclusion of water or air as, the first substance in concrete as the second substance.

Particularly preferred is the use of the apparatus as described in the field of medicine.

The frequency that is being used with the apparatus can generally range between 50 kHz to 500 MHz. The preferred range of frequency depends on the purpose of the measurement.

For example, if the apparatus is used for measuring the concentration of an ion in a liquid, such as the ion concentration in the dialysate of a patient, possibly with kidney disease, a frequency within a region of between 50 kHz to 250 kHz, preferably between 100 kHz to 200 kHz is used.

If the apparatus is used for measuring a liquid such as water in a solid, e.g. for measuring the humidity in a wall of concrete, sand, plaster and/or cement, a frequency within a frequency region of between 200 MHz to 500 MHz, preferably between 300 MHz to 400 MHz is used. It is also possible to measure air inclusions in a solid.

In a different application, if the apparatus is used for measuring the water concentration in a complex solution such as blood, a frequency in a region of between 100 MHz to 500 MHz is used, preferably between 300 MHz to 400 MHz.

If the apparatus used contains at least two independent resonance circuits with different length resonators, the dielectric property of the first substance can be determined dependent on the distance or position from the apparatus. Preferably, for such a use, the apparatus contains capacitors with a non-parallel geometry of its two electrodes, such that the composition comprising the first substance is introduced into the stray field of the capacitors. This depth measurement is based on the different geometry of the at least two capacitors, since the penetration depth of the field depends on a capacitor's geometry.

In a further aspect, the invention pertains to a method for determining the complex dielectric property of a known first substance that is part of a composition, wherein the composition comprises at least the known first substance to be measured and a second known substance. The method comprises or consists of the following steps:

Firstly, the composition that comprises the first substance of interest, is introduced at least in part into the field of a capacitor, such that the capacitor does not penetrate the composition (non-invasive measurement). The capacitor is part of an oscillator circuit that is coupled to a device for determining the resonance frequency, such as a frequency counter, of the oscillator circuit. The device for determining the resonance frequency is loosely coupled to the oscillator circuit, so that is does not influence its resonance frequency.

In a second step, the resonance frequency of the oscillator circuit is measured using the device for determining the resonance frequency.

In a third step, the complex dielectric property of the first substance is determined from the resonance frequency.

In a preferred embodiment of the method of the invention, the method further comprises the step of determining from the complex dielectric property a particle characteristic of the first substance chosen from the group consisting of particle density, mobility, and/or conductivity.

In another aspect, the invention pertains to the use of a method of the invention as described above and herein for determining the complex dielectric property of a known first substance in a composition that comprises at least the known first substance to be measured and a second known substance.

In FIG. 3a, the amplifying elements may be junction or field-effect transistors, vacuum tubes, operational amplifiers, or other types of amplifiers. The example diagram shows bipolar junction transistors (Q1, Q2). Three capacitors are shown: $C_1$ and $C_2$ are part of the actual astable multivibrator scheme, $C_{meas}$ is the capacitor into which the composition of interest is inserted to determine the dielectric property of the first substance that is connected to the two output terminals of the astable multivibrator; $R_1$ to $R_4$: resistors.

Figure 3B:
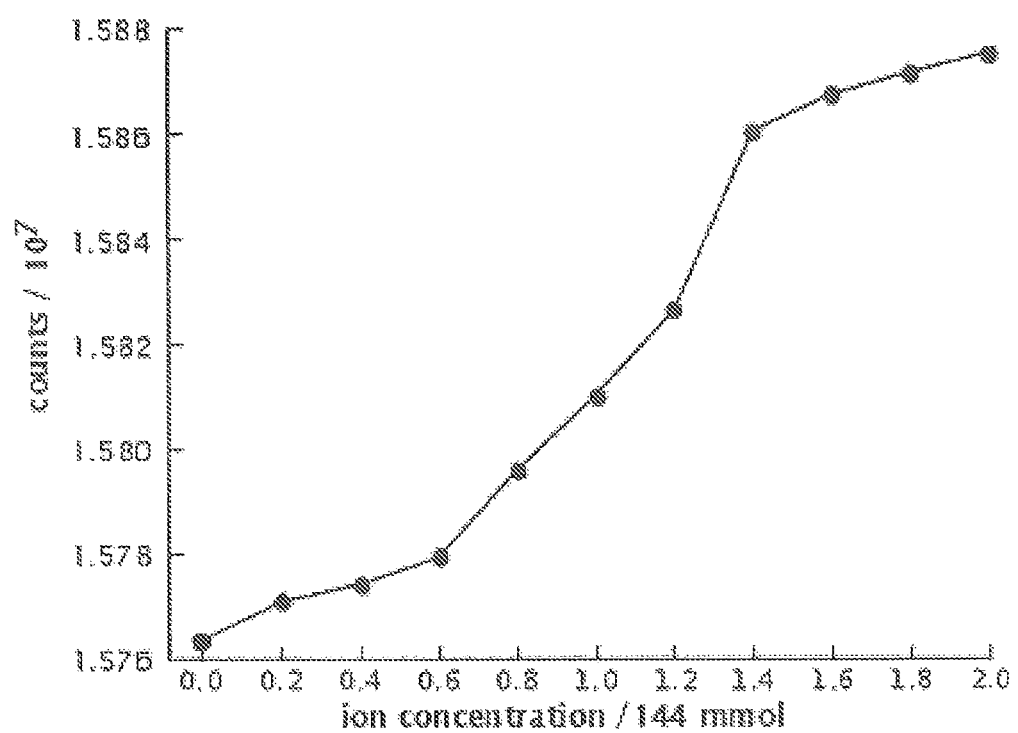
FIG. 3b is a graph showing the dependence of the reciprocal of the resonance frequency on the ion concentration according to an embodiment of the present invention.

FIG. 3b shows an example of a circuit diagram for the apparatus, in which an astable multivibrator is used (frequency counter not shown). The dependence of the reciprocal of the frequency of the ion concentration is depicted.

Figure 4:
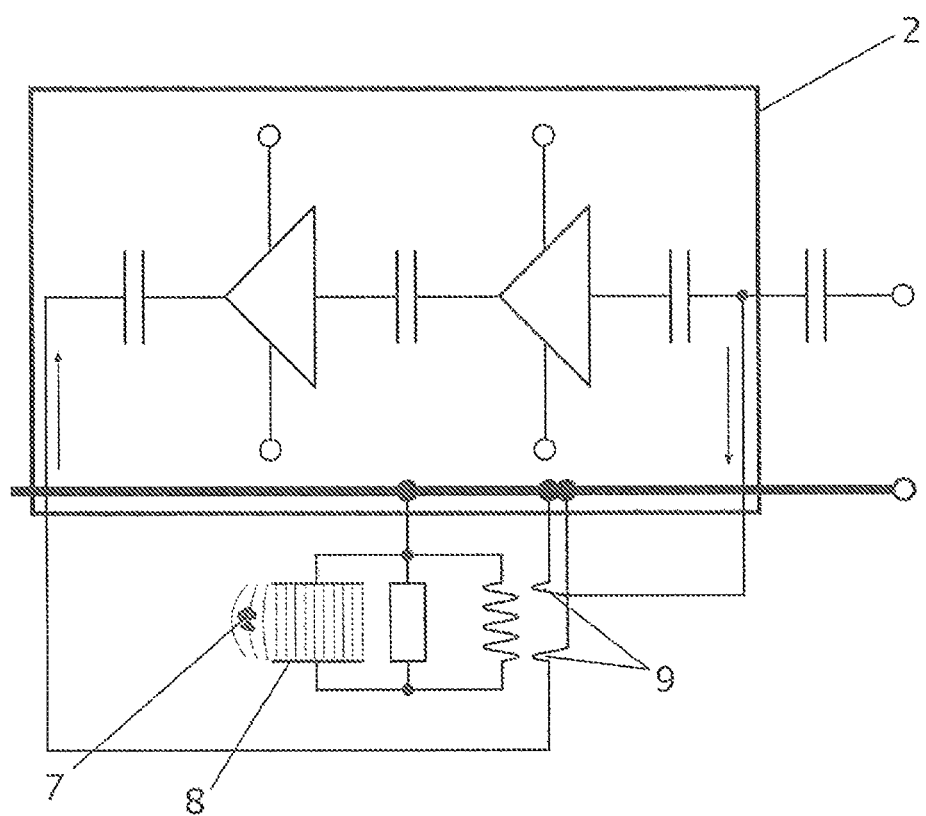
FIG. 4 illustrates an active coupling circuit according to an embodiment of the present invention.

FIG. 4 shows that when frequencies in the H-region are necessary to distinguish between different contributions to the dielectric value, the use of LC-circuits with high quality factors Q is preferred. Here, magnetically coupled coaxial cavities of lengths $\lambda/4$ yield Q-values up to 250, when converted to an oscillator by an active coupling circuit.

Figure 6:
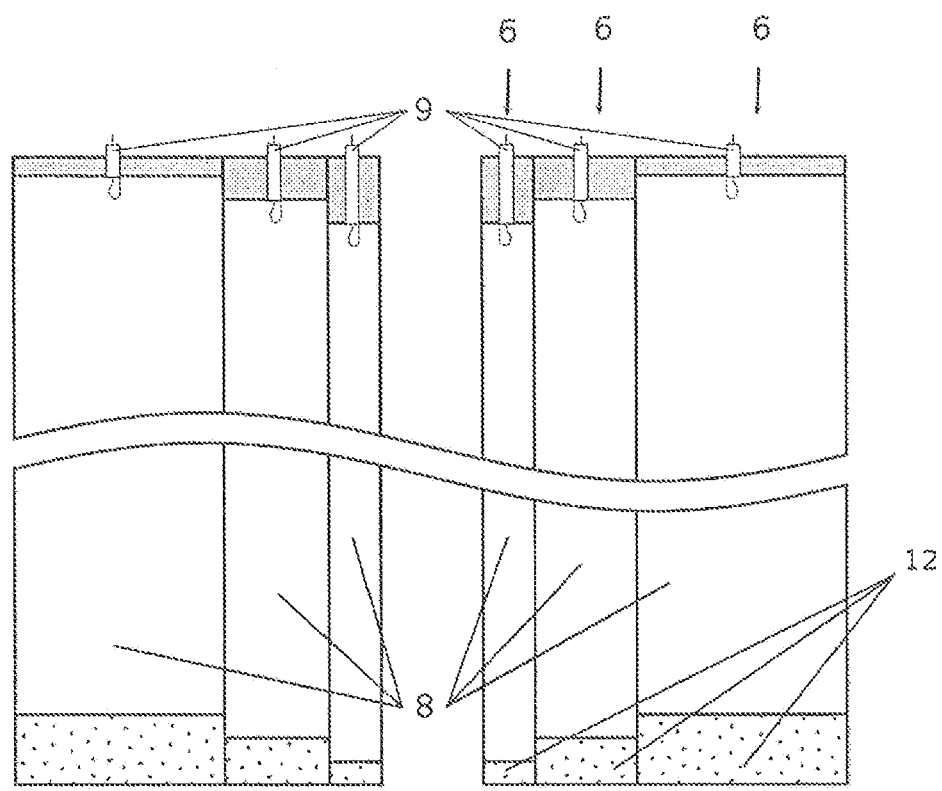
FIG. 6 shows a schematic depiction of a multiple-chamber resonator that comprises a multitude of resonators with different geometry according to an embodiment of the present invention.

In FIG. 6, the multiple-chamber resonator is useful for measuring depth dependent dielectric property values with a single measurement.

Figure 7:
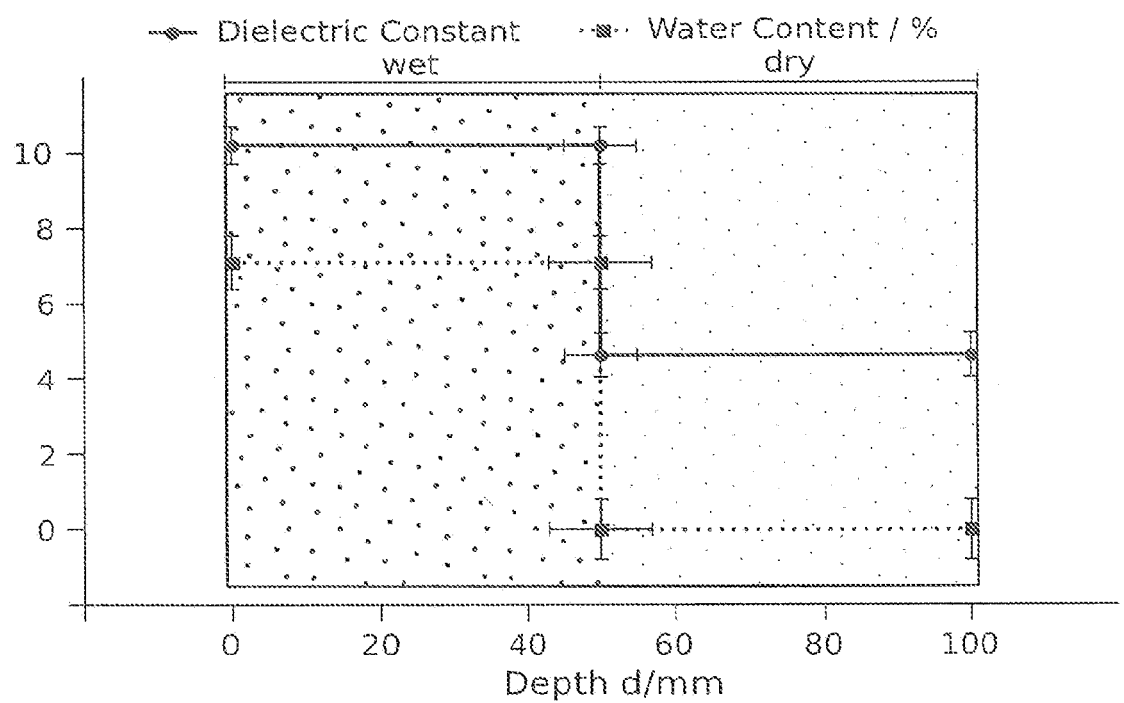
FIG. 7 is a graph showing a comparison of a measurement of the depth-dependent water content in a porous material (brick) according to an embodiment of the present invention.

In FIG. 7, a water-soaked brick with a thickness of 55 Mms is adjacent to a dry brick of same material and thickness.

Figure 8:
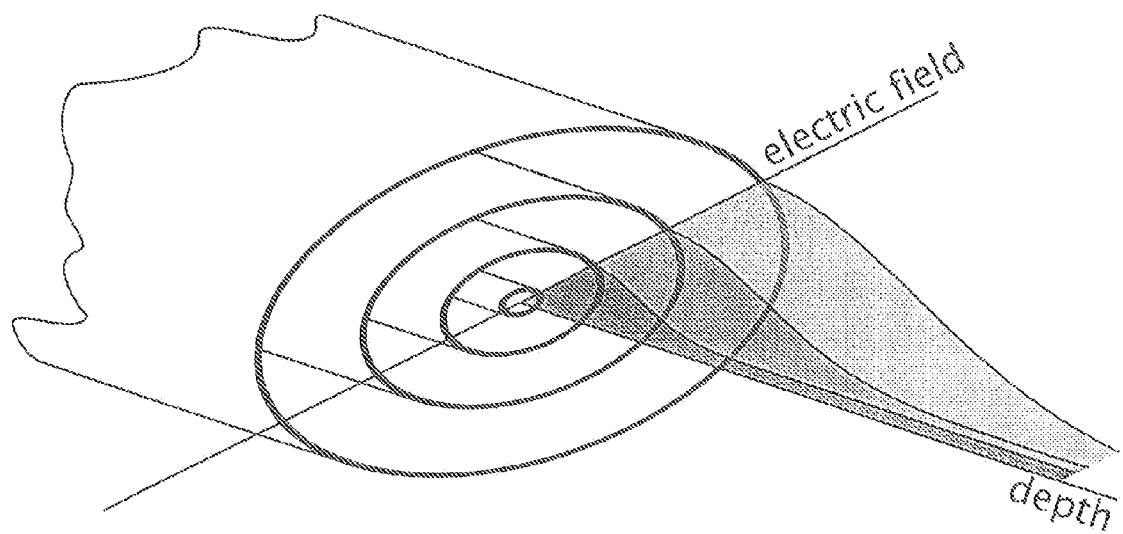
FIG. 8 shows an embodiment of the present invention in which three resonators with different geometries are coaxially positioned.

In FIG. 8, the embodiment is useful for measuring depth dependent dielectric property values with a single measurement, e.g. for measuring the content of water in a wall. It is shown in the figure that the electric fields caused by each resonator decreases with increasing distance from the end of the apparatus. In other words, the electric field changes differently for each of the three resonators used. From these three different courses any depth profile of water content which can be described by three parameters can be modeled.

Figure 9:
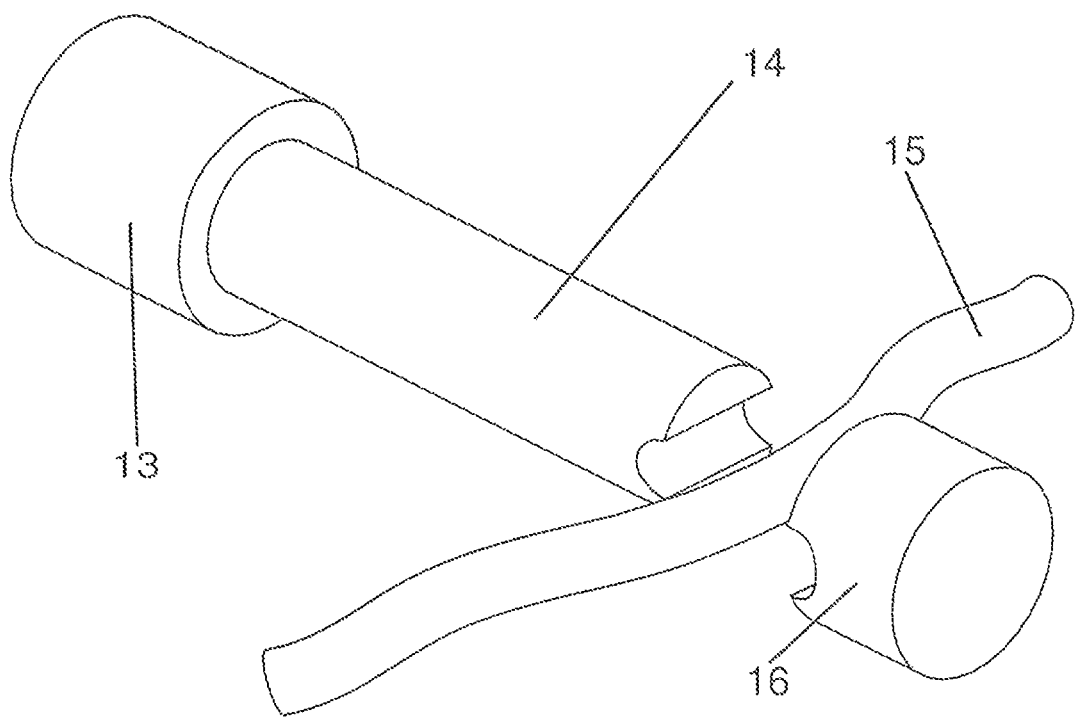
FIG. 9 shows an apparatus for determining a dielectric property according to an embodiment of the present invention.

In FIG. 9, the apparatus shown can be used in particular for determining a dielectric property of a known first substance in a liquid composition, the liquid composition comprising at least the known first substance to be measured and a second known substance. In one embodiment, the apparatus is used in a method for measuring the water content as the first substance of blood as the composition. In such a case, the blood present within a flexible tube or hose passes by a single resonator of the apparatus that forms a self-oscillating circuit together with an amplifier of the apparatus.

The invention refers to the measurement of resonance-frequency shifts as caused by changes of a dielectric value-dependent capacitance.

The capacitance of a capacitor is determined by the frequency-dependent complex dielectric value of a composition as the filling material of the capacitor. The description of the frequency-dependent dielectric value by the Debye equations takes into account the particle density, the particle mobility and a possible electric conductivity as well as the strength of permanent electric dipole moments. By an appropriate choice of a limited frequency range, a measurement of these quantities can be evaluated separately using the invention.

Figure 1B:
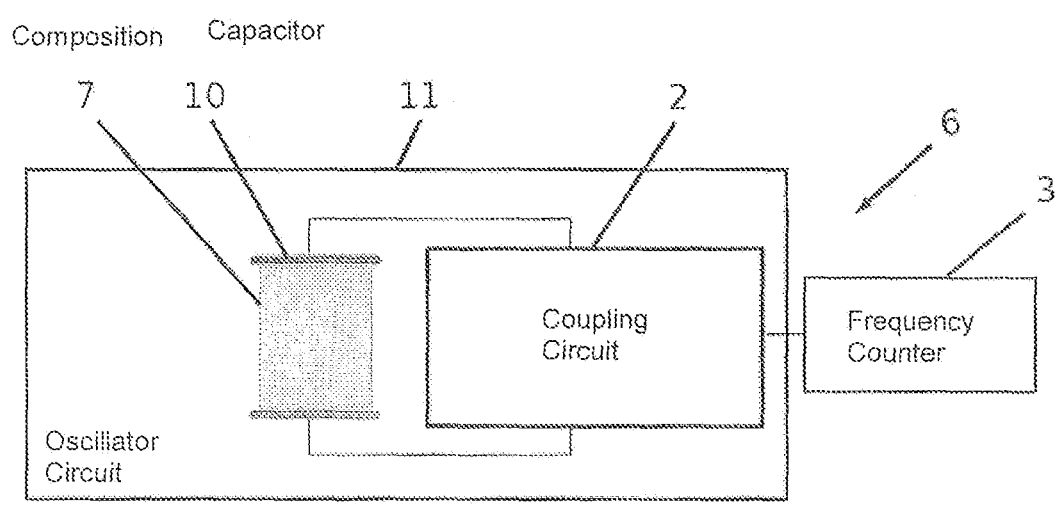
FIG. 1b shows a block diagram for a resonance circuit, wherein the capacitor is a parallel-plate capacitor according to an embodiment of the present invention.
Figure 1C:
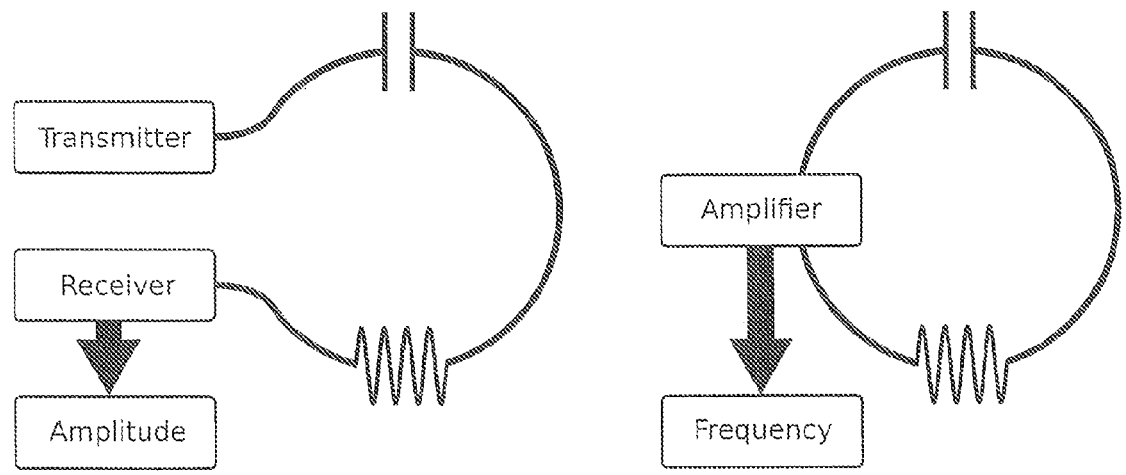
FIG. 1c shows an oscillator circuit according to the state of the art (left) and an oscillator circuit according to an embodiment of the present invention (right).

A capacitor 8, 10 containing the material to be investigated 7 (composition) is part of an oscillator circuit, the resonance frequency of which can be counted to high resolution. The oscillator circuit 11, as shown in FIGS. 1a and 1b, consists of a capacitor 8, 10 integrated into a coupling circuit 2. Coupling circuit 2 and capacitor 8, 10 together form an oscillating circuit 11.

FIG. 1b shows a preferred embodiment of the invention as shown in FIG. 1a, wherein the capacitor 10 is a plate capacitor with two electrodes that are positioned opposite and parallel to each other. In this case, the composition 7 comprising the first substance of interest is preferably inserted into the main field of the capacitor 10, which is located between the two electrodes of the capacitor 10, with the cylindrical surface connecting the outer edges of the electrodes defining the outer edge of the main field of the capacitor 10. In alternative applications, e.g. with capacitors 10 of different geometries, the composition may also be introduced into the stray field of the capacitor 10 or into both the main and the stray field of the capacitor 10.

A frequency counter 3, as shown in both FIGS. 1a and 1b, is loosely coupled to the oscillator circuit 11 and measures the resonance frequency of the oscillator circuit 11 when the composition 7 has been introduced at least in part into the field of the capacitor 10.

In contrast to oscillator circuits known from the state of the art, wherein the circuit comprises a transmitter and a receiver and wherein the amplitude is the parameter that is being determined (FIG. 1c, left), an oscillator circuit according to the present invention (FIG. 1c, right) is a self-oscillating circuit and the parameter that is being determined is a frequency.

The oscillator circuit 11 may be realized using an astable multivibrator-scheme or a parallel resonance scheme as an oscillation source for the oscillating circuit 11. An example of an astable multivibrator connected to a capacitor 8, 10 is shown in FIG. 3a.

The astable multivibrator shown in FIG. 3a is a regenerative circuit consisting of two amplifying stages connected in a positive feedback loop by two capacitive-resistive coupling networks. The amplifying elements may be junction or field-effect transistors, vacuum tubes, operational amplifiers, or other types of amplifier. The example diagram shows bipolar junction transistors.

Changes in the properties of the composition in the field of the capacitor cause changes in the capacitance of the capacitor 8, 10, and can thus be measured with high precision as frequency shifts of the resonance frequency of the oscillating circuit 11. In other embodiments, rather than measuring a shift of the resonance frequency, the resonance frequency of the oscillator circuit determined by the capacitor 8, 10 is measured only once, namely when the composition 7 within the field of the capacitor 8, 10 is known. The measurement of the change in frequency shift may allow for the determination of absolute values of the dielectric properties of the first substance, if at least two oscillation frequency values are determined that allow for the generation of a calibration function or calibration curve.

In contrast to reflection methods with transmitter and receiver circuits and small changes in amplitude of the backward wave amplitude measured by the receiver, an apparatus 6 with a circuit as shown in FIG. 1a overcomes the poor signal to noise ratio and yields a high accuracy of the results obtained therewith. As explained later, this general oscillator principle is used and/or adapted in preferred embodiments of the invention depending on the frequency region that is pre-selected to detect different characteristics of the particles, such as particle density, particle mobility, or particle conductivity.

As the capacitance is used as part of the oscillator circuit 11, the shift of the resonance frequency in this pre-selected frequency region reflects the influence of the parameters of interest, i.e. particle density, particle mobility, or particle conductivity.

The frequency is adapted depending e.g. on the length of the resonators used in the coupling circuit 2.

In contrast to reflection methods that provide these influences as small differences of large amplitudes, the invention provides these influences as frequency shifts that can be detected with far smaller uncertainties, even as small differences of large numbers. Therefore, the present invention, that is based on resonance measurements (i.e. time measurements) is an excellent tool for the measurement of particle characteristics in liquids, or liquid mixtures of liquid inclusions in solid materials.

Physical Basis of the Method

The frequency-dependent complex dielectric value $\in(f) = \in'(f) - i\in''(f)$ comprises the quantities $\in_\infty$ as contribution of the induced electric dipole moments, $\Delta\in_j$ as contribution of the permanent dipole moment of particles of species j with particle density $n_j$, $f_j$ as particle mobility frequency of species j and $\sigma$ as a possible electric conductivity of ionic particles in the composition:

$$\in'(f)=\in_\infty+\sum_j\Delta\in_j/(1+(f/f_j)^2),\ \in''(f)=\sigma/2\pi\in_0 f+\sum_j\Delta\in_j\cdot(f/f_j)/(1+(f/f_j)^2). \qquad (1)$$

Here, f is the variable frequency and $\in_0$ is the influence constant. The link between $\Delta\in$ and the particle density n is given by the relation $\Delta\in = np^2/3\in_0 kT$ with p as permanent electric dipole moment, k as Boltzmann's constant and T as absolute temperature. The conductivity $\sigma$ can be expressed by the ionic particle density $n_j$, if their mobilities $\mu_j$ are known: In the relation $\sigma = e_{0,j}\sum Z_j\mu_j n_j$ the quantity $e_0 \cdot Z_j$ is the charge of the individual ion.

The realization of the general circuit as shown in FIG. 1a and FIG. 1b depends on the frequency region that is to be pre-selected to detect different characteristics of the first substance of the composition.

Generally, the dielectric properties of the first substance of the composition can be measured when the dielectric properties of the other substances of the dielectric value are about one order of magnitude different. This allows for a determination of the dielectric properties of the first substance without interference from the other substances of the composition. The range of operation will now be explained in more detail with reference to FIG. 2, which shows the dielectric values $\in'$ and $\in''$ of the first and second substance of the composition depending on frequency.

Region H of FIG. 2

Whenever molecules with dipole moments and of small masses (e.g. water, methanol, ethanol, etc.) have to be measured as to their density—for instance water (as the first substance) in blood or ethanol (as the first substance) in diesel fuel—their mobility frequencies are so high that their dielectric answers can be separated from all other relaxations by the choice of a frequency region, preferably (200-400) MHz.

In FIG. 2, this region is indicated by the letter H for 'high'. The preferred embodiment of the apparatus used and of the method employed, then, is a quarter-wavelength coaxial resonator with a magnetically coupled coupling circuit 2 to make it an oscillator. In this case, the capacitor 8, 10 is preferably formed by the areas of the cut inner and outer conductors and the stray field in front of the open end of the resonator is the measuring field.

Region L of FIG. 2

If, for instance, the conductivity of the first substance in a composition is of interest—e.g. the conductivity of an ion-containing solution, such as a dialysate—the corresponding term in $\in''(f)$ in equation (1) has to be made prevailing all other terms. Therefore, In this case, the apparatus of the invention is preferred to comprise an astable multivibrator circuit. The capacitor 10 into which the composition is introduced into is preferably a two-plate arrangement part of the coupling circuit 2. The frequency region to be suited best for this purpose may be chosen to be (50-100) kHz, indicated by the letter L for 'low.

If the complex capacitance $C=C_0(\in'-i.\in'')$ is used as part of an astable multivibrator circuit, the period T of oscillation is determined by the quantities $C_m$, $R_m$ in the measuring branch and $C_c$, $R_c$ in the comparison branch to give a total value of $T=\ln(2)$ $(C_m R_m + C_c R_c)$. Choosing $C_m R_m = C_c R_c$ results in one half of the maximum possible influence of changes in $\in$ on changes in T (see FIG. 3a). The use of a multivibrator circuit is preferred when the frequency f has to be chosen in the above-defined region L. Here, an LC-circuit would give values of phase noise that are too high, as caused by a relatively low quality factor Q<50.

When frequencies in the H-region are necessary to distinguish between different contributions to the dielectric value, the use of LC-circuits with high quality factors Q is preferred. Here, magnetically coupled coaxial cavities of length $\lambda/4$ yield Q-values up to 250, when converted to an oscillator by an active coupling circuit, as depicted in FIG. 4.

Taken together, the present invention may comprise the following main features and exhibit the following main advantages:

1. The composition comprising the first substance to be measured becomes part of the circuit that is used for the measurement by introducing it at least in part into the field of the capacitor of the apparatus. No transmitter-receiver system is used.
2. A frequency is measured, not an amplitude, which allows for a more accurate determination of the dielectric properties of the first substance.
3. The electrodes of the capacitor do not touch the composition. In other words, the measurement is performed in a non-invasive manner.

REFERENCE SIGNS

1. Multiple-chamber resonator
2. Coupling Circuit
3. Frequency Counter
4. Computational unit
5. Display
6. Apparatus
7. Composition
8. Capacitor chambers
9. Coupling loops
10. Capacitor
11. Oscillator circuit
12. Dielectric material
13. Amplifier
14. Resonator
15. Hose/flexible tube
16. Metal object (metal cap)

Examples

This non-invasive method of measuring material characteristics via frequency shifts as described herein has been applied to solve questions from different fields:

If, for instance, the influence of electric conductivity of ions in solution has to be measured, the term $\sigma/2\pi\in_0 f = \alpha n/f$ can be made prevailing all other contributions for a reliable evaluation of the particle density n. Here, the frequency f in the denominator can be made sufficiently small to measure this contribution directly, i.e. approx 100 kHz. Such measurements rely on a multivibrator scheme as oscillation circuit.

Similar questions concerning the response of ions in solution can be answered by the use of the following physical principle: Water molecules from the compartment of 'free' water are trapped in the hydration shells of the ions with co-ordination numbers 8 to 12 (e.g., $Na^+$, $Cl^-$ in $H_2O$). These molecules in the 'loosely bound' phase have a mobility frequency $f_2 \ll f_1$ of the free water molecules. If the measuring frequency f is chosen to lie in between $f_1 < f < f_2$, the contribution of the free water compartment j=1 (see equation (1)) can be measured solely and with increasing particle density $n_2$, the influence on $\Delta\in_1$ is decreased to give the value $\Delta\in_1(n_2)=\Delta\in_1(0)(1-\beta n_2)$ with $\beta$ as fitting parameter to be calibrated. FIGS. 3a and 3b show an application example. FIG. 3b shows the dependence of the reciprocal of the resonance frequency on the ion concentration. Since this dependence is a monotonically increasing function, the ion concentrations can be determined in an unambiguous way.

In cases where no or only few ions (e.g. <0.1 mol) are present, for instance when determining the water concentration in blood or the ethanol content in diesel fuel, different mobilities can be the basis to separate the contributions of the molecules of interest with density $n_1$ and mobility $f_1$ in the presence of a larger amount of liquid partners with density $n_2$ and mobility $f_2 \ll f_1$. Here, the measured quantity $\Delta\in_1(n_1)$ is directly the desired value. FIG. 4 shows an application example; in the embodiment shown, the composition 7 is brought at least in part into the stray filed of the capacitor 8 of the apparatus 6.

If air or water inclusions in concrete or similar solid materials have to be detected, the dielectric value $\in_c$ of the concrete surrounding takes the role of the constant term $\in_\infty = 4.5$ to 5.5 and the deviation from this value yields the air- or water-content. In order to get information about the depth of such a disturbance, different measurements with coaxial resonators of different inner and outer diameters have to be carried out. If, for instance, the dependence of the dielectric value $\in$ on the depth d has to be approximated by a function $\in(d)$ with three fitting parameters, three different geometries of the coaxial resonators have to be used for measurements.

A preferred embodiment of the apparatus 6 of the invention was used to determine the dielectric properties of water as the first substance in concrete as the second substance, whereby water and concrete form a composition as defined above.

Figure 5:
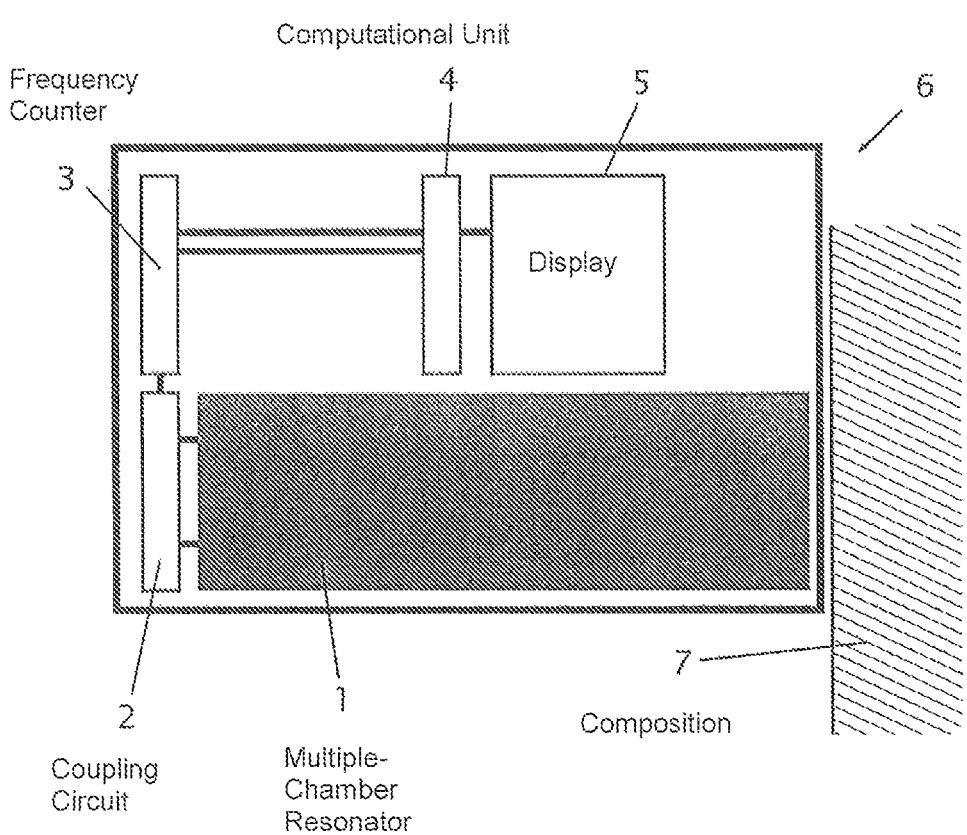
FIG. 5 shows a block diagram of an apparatus for the depth-dependent measurement of water in a wall according to an embodiment of the present invention.

The apparatus 6 is shown in FIG. 5 in a position for measuring the water content of a concrete wall 7. The oscillating circuit of the apparatus 6 consists of a plurality of capacitors 1 and a coupling circuit 2, which is shown in greater detail in FIG. 4. The plurality of capacitors 1 is a multi-chamber capacitor. The resonance frequency of the oscillating circuit is measured by a frequency counter 3 that is loosely coupled to the oscillating circuit. A computational unit 4 calculates from the measured resonance frequency the dielectric values of interest of the water (or, generally, of the first substance of interest) and this value of interest (or the probability of the value depending on the distance from the capacitor/apparatus) is being displayed numerically or graphically to a user on a display 5 of the apparatus 6.

FIG. 6 shows a plurality of capacitors 6 as a multi-chamber resonator 1 in greater detail. Three cylindrical lambda/4 resonator chambers are positioned coaxially and are each magnetically coupled to a separate resonance circuit. The resonators each have a different length, i.e. they are positioned adjacent to a dielectric material 12 of different thickness (see FIG. 5). The use of the multi-chamber capacitor allows the measurement of a depth profile without the need of making successive measurements with capacitors of different geometry.

A cavity resonator 8 is a short section of transmission line (e.g., a two-wire, coaxial or hollow pipe) of length l. An electromagnetic wave coupled into such a cavity resonator 8 is reflected at the ends and the resonance is a superposition of the partial waves. As the wavelength λ follows $l = n\lambda/4$, with $n = 1, 2, 3, \ldots$, the resonance frequencies are $f_n = n\,c/4\,l$, with c=velocity of light.

In the embodiment shown, one end of the cavity resonator 8 is closed for the magnetic coupling loops 9. At this end, the magnetic field B has its maximum; at the other end, which is open, the electric field has its maximum, creating the stray field into which the composition is to be brought at least in part. Oscillations for $n = 1, 3, 5, \ldots$ can therefore be observed. For example, with $l = 0.225$ m, the resonance frequencies are $$f_1 = 333 \text{ MHz}, f_3 = 1000 \text{ MHz}, f_5 = 3000 \text{ MHz}, \ldots$$

In order not to enter the region of beginning dielectric losses $\in''$ of water, only f1 can be used, thereby omitting the higher frequencies in the coupling circuit.

In such a cavity resonator the values of C, L and R are distributed over the whole length of the transmission line, with L (and thus B) having its maximum at the closed end and C (and thus E) having its maximum at the open end of the cavity. The Q values reached are $Q \approx 250$ for $f_1 \approx 350$ MHz.

Provided that the dielectric properties change following a step function depending on the depth, the dielectric properties can be described depending on the depth t as follows:

$$\in(d) = \in_N \text{ for } d < D, \in(d) = \in_F \text{ for } d \geq D,$$

with $\in_N, \in_F$ indicating the permittivity of the concrete near the resonator surface and far from it, respectively. Therefore, the parameters $\in_N, \in_F$, and D need to be determined. This can be achieved by using the definition of the average of $\in(d)$ with the electric field $E_j(t)$ of each resonator $j = 1, 2, 3$ as a weighting $$\in_j = \int\in(d)E_j(d)\delta d / \int E_j(d)\delta d,$$ with integrals from $d=0$ to $d=\infty$.

After simple transformations this results in $1/\in_j = 1/\in_F + (1/\in_N + 1/\in_F)f_j(D)$ with $f_j(D)$ determined by the different resonator-geometries.

In case $\in_N > \in_F$ the water is near the surface and the following applies:

$$\in(d=0) = p\in_W + (1-p)\in_C$$

$$\in(d \to \infty) = \in_C.$$

Where p is the fraction of water in the concrete.

In case $\in_N < \in_F$ the water is far from the surface and the following applies:

$$\in(d=0) = \in_c,$$

$$e(d \to \infty) = p\in_W + (1-p)\in_c.$$

With the know value for water, $\in_W = 81$, the $\in$ value of the concrete can be obtained and the volume proportion of water dependent on the depth from the point of measurement into the wall.

Before the actual measurement, it is recommended to make a measurement with only with air being in the field of the capacitor in order to calibrate. An example is shown in FIG. 7: Here, the measured results are compared to the known Parameters a, b, D of the experimental setup: A water-soaked brick with a thickness of 55 Mms is adjacent to a dry brick of same material and thickness. The comparison shows that the method is capable of determining the correct depth of the beginning of the water-soaked area.

FIG. 8 shows an embodiment of the invention, in which three resonators with different geometry are coaxially positioned. All three resonators are of cylindrical shape. The resonator with the smallest diameter is located in the center of the multi-chamber resonator. In a coaxial fashion, a second resonator of cylindrical shape, and a third resonator of cylindrical shape are coaxially positioned to the first resonator, wherein the diameter of the second resonator is larger that that of the first resonator, and the third resonator has a diameter that is larger than the diameter of the second resonator.

The coaxial arrangement of the resonators allows for the determination of a material property of the first substance of a composition in a rotationally symmetric manner. By scanning a surface of interest in the direction of two axes within the surface, wherein the two axes are non-identical, preferably perpendicular to each other, each measuring point can be accurately determined.

Such an embodiment is useful for measuring depth dependent dielectric property values with a single measurement, e.g. for measuring the content of water in a wall (cf., e.g., FIGS. 6 and 7). As can be seen in FIG. 8, the electric field decreases for each resonator of the apparatus for determining a dielectric property with increasing distance from the end of each of the three resonators of the apparatus in different but well known behaviors: The point where the field has decreased to one half of its initial value is closely connected to the geometry of each resonator. In other words, the electric field changes differently for each of the three resonators used due to different properties of the resonators. When measuring the resonance frequency of the oscillator circuit of the apparatus shown in FIG. 8 (comprising a multi-chamber resonator with at least three resonators) and determining from the resonance frequency the complex dielectric property of a first substance that is to be measured in a composition also comprising at least a second substance, then the resonance frequency yields the dielectric property. Thus, the complex dielectric property of the first substance can be determined with just one measurement.

The use of nested resonators allows, due to different half value depths of the stray field, to determine a depth resolution of the first substance of the composition that is measured.

The coaxial arrangement of resonators, in particular of two or more resonators, preferably of three resonators, ensures that all chambers of the resonators are subject to the same temperature differences that might change the length of the chambers. Therefore, such temperature factors could be taken into account by calibrating the apparatus in air.

A means for analyzing the measured resonance frequency of the oscillator circuit, such as a microprocessor, allows for determining a difference between six depth profiles of water in a solid material, such as water in concrete that each are defined by three parameters, namely increasing or decreasing exponential behavior, describing either a high moisture concentration at the surface decreasing towards the inner part of the concrete or vice versa.

increasing or decreasing step function in an appropriate depth, describing either a high moisture concentration at the surface with a n abrupt decrease at a certain depth or vice versa, and increasing or decreasing rectangular function in a given depth, describing a small region with high/low moisture concentration at a certain depth.

The apparatus shown in FIG. 9 is suitable for determining a dielectric property of a first substance in a composition in a non-invasive manner. The apparatus shown comprises a capacitor (not shown) for creating a field into which the composition can be introduced at least in part, wherein the capacitor is part of a self-oscillating oscillator circuit, and further comprises a device for determining the resonance frequency of the oscillator circuit.

The apparatus shown in FIG. 9 can be used in a method for measuring the content of a first substance, such as water, in a composition, such as blood. In particular, the embodiment shown is useful if the composition is a liquid. A hose or flexible tube (15) transports a liquid composition, such as blood along the open end of a single resonator (14) as described in example 8. The resonator (14) and an amplifier (13) together form a self-oscillating circuit. A metal object (16), such as a metal cap positioned at the hose (15) helps to avoid external signals that could disturb the measurement. The water-content is measured in the same way as with the device to measure e.g. the water-content of concrete as described above (i.e. with a stray filed), except that no depth information is needed because the water is equally distributed inside the blood. Thus, the device may only comprise a single resonator (14) in one embodiment of the invention.

Specifically, the flexible tube (15) is brought into the field of the capacitor. In the embodiment shown, the stray field is used for the measurement. The capacitor does not penetrate the composition in the flexible tube (15). Subsequently, the resonance frequency of the self-oscillating oscillator circuit is measured and from the resonance frequency the complex dielectric property of the first substance is determined.

The embodiment shown can also be used, e.g. if the composition to be measured needs to remain sterile, which is often the case for blood of a subject, because the composition does not come into direct contact with the apparatus of the invention, since a stray field is used for the measurement.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

The invention claimed is:

1. A method for determining a dielectric property of a first substance in a composition, comprising:

providing a composition comprising at least the first substance and a second substance;

introducing the composition at least in part into a field of a capacitor, such that the composition is electrically isolated from electrodes of the capacitor, wherein the capacitor is part of an oscillator circuit coupled to a device for determining a resonance frequency of the oscillator circuit;

measuring a resonance frequency of the oscillator circuit;

determining a dielectric property of the first substance from the resonance frequency;

wherein measuring the resonance frequency of the oscillator circuit comprises:

determining a first resonance frequency of the oscillator circuit when only the first substance is introduced at least in part into the field of the capacitor; and determining a second resonance frequency of the oscillator circuit when only the second substance is introduced at least in part into the field of the capacitor; and determining a calibration function from the first and second resonance frequencies.

2. The method of claim 1, further comprising:

determining an absolute value of the dielectric property of the first substance using the calibration function.

3. The method of claim 1, further comprising determining a particle characteristic of the first substance from the dielectric property.

4. The method of claim 3, wherein the particle characteristic is chosen from the group consisting of a particle density, a particle mobility and a particle conductivity.

5. The method of claim 1, wherein the first substance is a liquid.

6. The method of claim 5, wherein the second substance is a liquid or a solid.

7. The method of claim 1, further comprising determining, from the dielectric property of the first substance, a content of water in blood of a patient, wherein the water is the first substance and the blood is the second substance.

8. The method of claim 1, further comprising determining, from the dielectric property of the first substance, a concentration of an ion in a dialysate, wherein the ion is the first substance and the dialysate is the second substance.

9. The method of claim 1, further comprising determining, from the dielectric property of the first substance, a content of ethanol in diesel fuel, wherein the ethanol is the first substance and the diesel fuel is the second substance.

10. The method of claim 1, further comprising determining, from the dielectric property of the first substance, an inclusion of water or air in concrete, wherein the water or the air is the first substance and the concrete is the second substance.

* * * * *